United States Patent [19]

Porteous et al.

[11] Patent Number: 4,648,906
[45] Date of Patent: Mar. 10, 1987

[54] HIGH STRENGTH DENTAL IMPRESSION COMPOSITION

[75] Inventors: Don D. Porteous, Los Angeles; Ornan Valle, Culver City, both of Calif.

[73] Assignee: Van R Dental Products, Inc., Los Angeles, Calif.

[21] Appl. No.: 865,114

[22] Filed: May 20, 1986

[51] Int. Cl.$^4$ ................................................ C09K 3/00
[52] U.S. Cl. ...................................... 106/35; 106/208; 106/209; 433/214

[58] Field of Search .......................... 106/35, 208, 209; 523/109; 433/214

[56] References Cited

U.S. PATENT DOCUMENTS 4,242,239 12/1980 Kessler et al. ...................... 523/109

Primary Examiner—Lorenzo B. Hayes
Attorney, Agent, or Firm—Louis J. Bachand

[57] ABSTRACT

A dental impression composition is provided which has high tensile and gel strengths, but an absence of graininess through the use of zinc borate and a water soluble alkylene glycol in the composition.

16 Claims, No Drawings

HIGH STRENGTH DENTAL IMPRESSION COMPOSITION

TECHNICAL FIELD

The present invention has to do with dental impression materials, namely reversible hydrocolloid gel compositions having improved strength properties by virtue of the use of zinc borate in reversible hydrocolloid gel compositions containing water soluble alkylene glycols.

BACKGROUND OF THE INVENTION

In dental practice the professional uses impression materials to obtain impressions of teeth which are then used to mold caps, crowns and inlays, or other prosthesis. Precision of impression molds is a paramount consideration for comfort of the prosthesis. Realizing precision of impression is dependent on obtaining a good impression in the first place, and maintaining the good impression and this requires high gel strength and tensile strength in the gelled impression composition during removal from the teeth and through use in the forming the plaster from which the prosthesis is to be made.

Many dentists prefer the use of reversible hydrocolloid gels as impression compositions which are unparalled for accuracy. These gels are obtained by mixing water and a gel base such as agar-agar, and tempering the gel in a conditioning bath until used.

The following patents relate to reversible hydrocolloid gel impression materials, and have been considered in preparing this application: U.S. Pat. No. 2,021,059 to Harrison; U.S. Pat. No. 2,089,552 to Harrison; and, U.S. Pat. No. 2,234,583 to Preble. The first two of these patents teach the use of glycerol in hydrocolloid compositions, but such systems require a higher temperature tempering bath to avoid loss of workability, and thus a pre-application conditioning step, while the last of these patents teaches that an increase in strength of reversible hydrocolloid gel materials is realized by the use of borates, but such systems as are taught are grainy, lumpy, and too viscous for utility as impression materials.

SUMMARY OF THE INVENTION

It is an object of the present invention to provide a high gel strength, high tensile strength dental impression composition.

This and other objects of the invention to become apparent hereinafter are realized in accordance with the invention in the high gel strength, high tensile strength dental impression composition consisting essentially of a reversible hydrocolloid gel forming base, and an aqueous reagent in an amount sufficient to form a reversible gel with said base, said reagent comprising from 50 to 95% by weight water and the balance a water soluble glycol, and zinc borate in an amount above about 0.001 part per 100 parts by weight of the composition and less than that making the composition lumpy or grainy.

In particular embodiments, the gel forming base is agar-agar; the composition is free of glycerine; the weight ratio of aqueous reagent to gel forming base is between 8 and 12; and the zinc borate is present in an amount between about 1 and 7 parts per 100 parts by weight of the composition.

In a more particular embodiment, there is provided a high gel strength, high tensile strength dental impression composition consisting essentially of a reversible hydrocolloid gel forming base, an aqueous reagent in an amount equal to the amount of water sufficient to form a reversible gel with the base, the reagent comprising a major weight amount of water and the balance a water soluble alkylene glycol, and zinc borate in an amount between 0.1 and 5 parts per 100 parts by weight of the composition.

In this and like compositions, typically, the weight ratio of alkylene glycol to gel base in said composition is between 1.5 and 5.0; the gel forming base is agar-agar; the alkylene glycol has from 1 to 6 carbon atoms, and the composition is free of glycerine; the weight ratio of aqueous reagent to gel forming base is between 8 and 12; the zinc borate is present in an amount less than that contributing a grainy texture to the composition; the alkalene glycol is dipropylene glycol; and the zinc borate is present in an amount of from 0.3 to 2.5 parts per 100 parts of the composition.

In a highly particularly preferred embodiment, the composition consists essentially of from 8 to 12 parts agar-agar, from 60 to 80 parts water, from 15 to 30 parts water soluble dialkylene glycol, and from 0.3 to 2.5 parts of zinc borate, per 100 parts by weight of the composition, and the alkylene glycol is dipropylene glycol.

The invention further contemplates the method of increasing the gel strength and tensile strength of reversible hydrocolloid compositions comprising a reversible hydrocolloid forming base and water sufficient to form a gel with the base, including incorporating in the composition from 0.001 to 5 parts of zinc borate per 100 parts by weight of the composition and sufficient water soluble alkylene glycol to prevent graininess in the composition.

DETAILED DESCRIPTION

As noted above, the present composition includes a reversible hydrocolloid gel forming base and an aqueous reagent. The base is typically agar-agar, but may be any of the gel forming materials known in the art including Irish moss, Iceland moss, etc. The aqueous reagent comprises water and the water soluble alkylene glycol, such as ethylene glycol, diethylene glycol, propylene glycol, dipropylene glycol, and the like up to about 6 carbon atoms. The reagent typically comprises from 50 to 95% by weight water and the balance the alkylene particularly dipropylene glycol, with preferred proportions being 65 to 75 weight percent water and conversely 35 to 25 weight percent of the glycol. The aqueous reagent is preferably free of glycerine which has been found to disadvantageous in formulating a composition owing to its tendency to result in a composition which is temperable not at a low range of about 130° F. but only at about 150° F.

The aqueous reagent is typically present in an amount of 8 to 12 parts by weight per part of gel forming base, and preferably about 10 parts per part of base, with the weight ratio of alkylene glycol to gel base in the composition being in the 1.5 to 5 range and preferably about 2.5 to 3.5.

Zinc borate has been found to be especially effective in contributing gel strength and tensile strength to the gelled product, which makes the product resistant to tearing and otherwise failing after being molded to the tooth surface, regardless of undercuts and thinned sections, when present in the above amounts. It has been noted that undue graininess and lumpiness in the composition which preclude a faithful impression are avoided despite the presence of the insoluble zinc borate when an alkylene glycol is used in the composition. The use of the glycerine in the composition does not provide the same benefit of reduction in graininess, absence of lumpiness and improved workability obtained with the alkylene glycols.

The combination of zinc borate and alkylene glycols, particularly dipropylene glycol, with agar-agar gel forming base in the just discussed proportions has been found to provide a uniquely advantageous hydrocolloid dental impression material with nearly ideal properties of gel strength (improved about 30% over glycerine formulas), tensile strength (improved about 30% over glycerine formulas) tempering ability (130° F. vs. 150° F. for glycerine formulas), grain and lump reduced texture and workability is dramatically better than glycerine formulas at the cooler temper, and accuracy of impression particularly at undercuts is heightened.

EXAMPLE 1

A typical composition according to the invention is prepared by placing the following materials in a suitable heated vessel: 140 parts by weight of agar-agar melted in 1400 parts of boiling water; a thickener at 10 parts and dissolved into the agar-agar water mixture; zinc borate at 1.5 parts predispersed in a minimum amount of water; and dipropylene glycol to reduce graininess: about 50 parts by weight, with flavoring and colorant if desired and the entire mass blended until uniform and then the mixture is put up in small tubes for use by the dentist.

The composition in tests exhibits a resistance to tearing when being removed from typodonts or actual teeth, even from undercut areas and in thinned sections which is superior to non-zinc borate compositions otherwise similar, and this is indicative of high gel strength and high tensile strength.

EXAMPLE 2

Example 1 is duplicated but using propylene glycol in place of the dipropylene glycol, and at 350 parts rather than 50. Results are similar with an evident increase in gel strength and tensile strength over a comparable non zinc borate system.

CONTROL

Example 1 is duplicated using glycerine in place of the dipropylene glycol. The composition is to grainy and lumpy and has to high viscosity for successful application to teeth. Moreover, what gelled material is obtained is low in gel and tensile strength and prone to tearing. It is also reported that the glycerine containing composition has to be tempered at 150° F. rather than about 130° F. or viscosity build-up through progressive gelation makes the composition too difficult to apply.

We claim:

1. High gel strength, high tensile strength dental impression composition consisting essentially of a reversible hydrocolloid gel forming base, and an aqueous reagent in an amount sufficient to form a reversible gel with said base, said reagent comprising from 50 to 95% by weight water and the balance a water soluble glycol, and zinc borate in an amount above about 0.001 part per 100 parts by weight of the composition.

2. High gel strength, high tensile strength dental impression composition according to claim 1, in which said gel forming base is agar-agar.

3. High gel strength, high tensile strength dental impression composition according to claim 1, in which said composition is free of glycerine.

4. High gel strength, high tensile strength dental impression composition according to claim 1, in which the weight ratio of aqueous reagent to gel forming base is between 8 to 12.

5. High gel strength, high tensile strength dental impression composition according to claim 1, in which said zinc borate is present in an amount between about 1 and 7 parts per 100 parts by weight of the composition.

6. High gel strength, high tensile strength dental impression composition consisting essentially of a reversible hydrocolloid gel forming base, an aqueous reagent in an amount equal to the amount of water sufficient to form a reversible gel with said base, said reagent comprising a major weight amount of water and the balance a water soluble alkylene glycol, and zinc borate in an amount between 0.1 and 5 parts per 100 parts by weight of the composition.

7. High gel strength, high tensile strength dental impression composition according to claim 6, in which the weight ratio of alkylene glycol to gel base in said composition is between 1.5 and 5.0.

8. High gel strength, high tensile strength dental impression composition according to claim 7, in which said gel forming base is agar-agar.

9. High gel strength, high tensile strength dental impression composition according to claim 8, in which said alkylene glycol has from 1 to 6 carbon atoms, and in which said composition is free of glycerine.

10. High gel strength, high tensile strength dental impression composition according to claim 8, in which the weight ratio of aqueous reagent to gel forming base is between 8 and 12.

11. High gel strength, high tensile strength dental impression composition according to claim 10, in which said zinc borate is present in an amount less than that contributing a grainy texture to the composition.

12. High gel strength, high tensile strength dental impression composition according to claim 11, in which said alkalene glycol is dipropylene glycol.

13. Low temperature tempering, high gel strength, high tensile strength dental impression composition according to claim 12, in which said zinc borate is present in an amount of from 0.3 to 2.5 parts per 100 parts of the composition.

14. High gel strength dental impression composition consisting essentially of from 8 to 12 parts agar-agar, from 60 to 80 parts water, from 15 to 30 parts water soluble dialkylene glycol, and from 0.3 to 2.5 parts of zinc borate, per 100 parts by weight of the composition.

15. High gel strength, high tensile strength dental impression composition according to claim 14, in which said alkylene glycol is dipropylene glycol.

16. Method of increasing the gel strength and tensile strength of reversible hydrocolloid compositions comprising a reversible hydrocolloid forming base and water sufficient to form a gel with said base, including incorporating in said composition from 0.001 to 5 parts zinc borate per 100 parts by weight of the composition and sufficient water soluble alkylene glycol to prevent graininess in said composition.

* * * * *